United States Patent [19]

Larock

[11] 4,351,949

[45] Sep. 28, 1982

[54] BICYCLIC PROSTAGLANDIN ANALOGS AND METHOD OF SYNTHESIS

[75] Inventor: Richard C. Larock, Ames, Iowa

[73] Assignee: Iowa State University Research Foundation, Inc., Ames, Iowa

[21] Appl. No.: 231,596

[22] Filed: Feb. 5, 1981

[51] Int. Cl.$^3$ ........................................... C07C 177/00
[52] U.S. Cl. .................................... 548/359; 560/118; 560/120; 562/500; 562/502; 564/188; 568/665; 568/820; 260/429 L
[58] Field of Search .................... 260/429 L; 560/118, 560/120; 562/500, 502; 548/359; 564/188; 568/665, 820

[56] References Cited

U.S. PATENT DOCUMENTS 4,113,755  9/1978  Larock ........................... 260/429 L Primary Examiner—Robert Gerstl
Attorney, Agent, or Firm—Zarley, McKee, Thomte, Voorhees & Sease

[57] ABSTRACT

New organopalladium reactions involving the addition of pi-allylpalladium compounds to strained bicyclic alkenes, and subsequent chain extension reactions employing the chemistry of organopalladium compounds are disclosed. By these techniques a large number of bicyclic prostaglandin analogs are prepared, which are useful as inhibitors of arachidonic acid induced platelet aggregation, and are specific inhibitors of thromboxane synthetase.

7 Claims, No Drawings

BICYCLIC PROSTAGLANDIN ANALOGS AND METHOD OF SYNTHESIS

GRANT REFERENCE

The invention described herein was made in the course of work under a grant from the National Institutes of Health, No. AM 21795.

BACKGROUND OF THE INVENTION

The mammalian hormones known as prostaglandins are an extremely important, biologically active class of C-20 unsaturated hydroxy acids first discovered in the 1930's. They have been found to have pronounced effects on the cardiovascular, respiratory and renal systems; the gastrointestinal tract; blood platelets and bone; the eye, skin, lungs, and the reproductive organs. They appear to have pharmacological potential in the treatment of nasal congestion, stomach ulcers, hypertension, asthma, inflammation and thrombosis, as well as possible use in the induction of labor, termination of pregnancy, and utility in contraception. To date the major drawbacks to clinical application of the prostaglandins have been the very broad range of physiological activity prevalent in these compounds and their brief duration of action due to rapid metabolic deactivation. The desire for longer lasting drugs exhibiting much more specific activity has recently produced a number of very interesting analogs of prostaglandins and many structure-activity studies have resulted.

Tremendous potential also exists in the development of prostaglandin antagonists and reagents which will inhibit prostaglandin biosynthesis and metabolism. For this reason there has been considerable work of late on the biosynthetic pathways involved in the formation of prostaglandins. This work has resulted in the recent discovery of intermediate prostaglandin endoperoxides and their biosynthetic products prostacyclin and the thromboxanes.

As biologically potent substrates, as well as key intermediates in prostaglandin biosynthesis, the endoperoxides have stimulated considerable recent synthetic effort. Some of these compounds are potent vasoconstrictors, stimulate smooth muscle contraction, induce the aggregation of human blood platelets, and inhibit $PGE_1$, $PGE_2$ and thromboxane biosynthesis.

With the recent discoveries of the highly active but very unstable prostacyclin and thromboxanes, attention has turned towards the synthesis of stable analogs of these compounds. Numerous prostacyclin analogs possessing substantial biological activity are now known. Similarly, the potent blood platelet aggregating and vasoconstrictor properties of thromboxane $A_2$ ($TXA_2$) have inspired other workers to synthesize each of the following stable analogs:

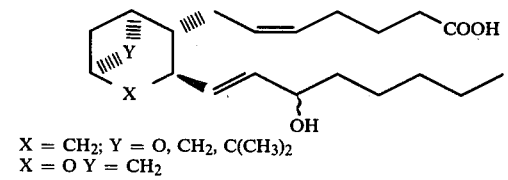

X = $CH_2$; Y = O, $CH_2$, $C(CH_3)_2$
X = O  Y = $CH_2$

These compounds are inhibitors of $PGH_2$-induced aggregation of human blood platelets; have shown very potent vasoconstricting activity as well as behavior as a potent thromboxane $A_2$ antagonist on platelet aggregation, while selectively inhibiting the biosynthesis of thromboxanes; and selectively inhibit coronary artery constriction, platelet aggregation and thromboxane formation. The compound with X=$CH_2$, Y=$C(CH_3)_2$ has been suggested as a suitable antithrombotic agent.

From the above brief review, it should be quite obvious that the natural prostaglandins, the endoperoxides, prostacyclin and the thromboxanes display an extraordinary range of biological activity. The synthesis of stable analogs of these compounds shows tremendous promise of providing new compounds with more specific activity which will prove useful in the treatment of a vast array of human physiological ailments. Most syntheses to date have involved lengthy multi-step sequences or have begun with the natural prostaglandins.

The primary objective of the present work is directed towards the development of entirely new synthetic routes to compounds of the type previously mentioned—routes which greatly shorten the present procedures, as well as provide a large number of new compounds, particularly bicyclic prostaglandin analogs prepared by the addition of pi-allylpalladium compounds to strained bicyclic alkenes.

A further object is to prepare certain compounds of the type previously described which show substantial inhibition of arachidonic acid induced blood platelet aggregation and which appear to be very specific inhibitors of thromboxane synthetase.

The method, compounds and manner of performing the reactions and accomplishing the objectives of this invention are illustrated by the detailed description which follows hereinafter.

DETAILED DESCRIPTION OF THE INVENTION

The present invention relates to novel prostaglandin endoperoxide analogs, and to their production and use.

More particularly, this invention relates to novel bicyclic prostaglandin analogs, to pharmaceutical compositions containing at least one of the compounds, and to a process for the preparation of the compounds. The novel compounds of this invention are represented by the following formula:

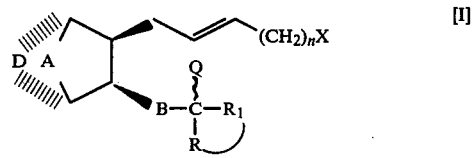

wherein n equals a whole integer of from 0 to 7, X is carboxylic acid, or $C_1$–$C_8$ ester, alcohol, ether, or amide groups; A is methylene, ethylene, oxy, imino, or lower alkyl, phenyl or aryl substituted imino; D is methylene, ethylene, vinylene, methyleneoxy, alkylidenedioxy, iminooxy, dithio, or azo; B is ethylene, cis and trans vinylene and ethynylene; R and $R_1$ are hydrogen, lower alkyl and lower aryl or $(CH_2)_Z$ with Z being 2 to 5, and Q is hydroxy, methoxy, acetoxy or hydrogen, or Q and R are both oxa.

In the significance as used above, it is possible for "n" to be from 0 to 12; however, since in the natural prostaglandins "n"=3, it has been found that the more one moves away from 3, the more unlikely that the compounds would have any specific activity. 0 to 7 are preferred with the most preferred being from 1 to 5, since this most nearly brackets, on both sides, the natural biologically active compounds.

The moiety represented by X is the easiest to change in the structure. It is not critical to the process or the products of this invention, and can be changed by conventional, routine chemistry. Most preferred is a carboxylic acid group since once again the natural prostaglandins have a carboxylic acid group at the X position. With other functional groups such as esters, alcohols, ethers and amides, preferably $C_1$ to $C_8$ groups are employed, and most preferably $C_1$ to $C_5$. "A" is preferably methylene or ethylene, but can also be oxygen, imino, or lower alkyl, phenyl or aryl substituted imino groups. The term "lower" refers to having from $C_1$ to $C_8$.

"B" can be ethylene, cis and trans vinylene, and ethynylene. Since the natural prostaglandin compounds are the trans vinylene compounds, it may be more desirable to prepare the trans compounds; however, the cis compounds and ethynylene compounds also have substantial biological activity and can be prepared equally as satisfactorily.

"D" can be methylene, ethylene, vinylene, methyleneoxy, alkylidenedioxy, iminooxy, dithio or azo. D is preferably ethylene or vinylene. "R" and "$R_1$" are hydrogen, lower alkyl and lower aryl, or $(CH_2)_z$, with Z being 2 to 5. The term "lower" is used in the same sense as previously defined.

Finally, "Q" is selected from the group consisting of hydroxy, methoxy, acetoxy, or hydrogen, or Q and R are both oxa. The compounds [I] have been found to possess the property of exhibiting substantial inhibition of arachidonic acid induced platelet aggregation. Moreover, some of them appear to be highly specific inhibitors of thromboxane synthetase. That is, they inhibit blood clotting in a very effective manner. Tests demonstrating this will be hereinafter described.

The method of synthesis of these prostaglandin analogs can be generally summarized as an addition reaction of a pi-allylpalladium compound to bicyclic alkenes. More particularly, as a starting material a terminal olefin is converted to a pi-allylpalladium compound in a first step. Thereafter, the pi-allylpalladium compound is added to a bicyclic olefin to provide an addition compound, from which the palladium moiety is displaced by an acetylene or vinyl moiety, to provide the basic skeletal structure of [I]. Finally, protecting groups, if any, can be removed from the acetylene moiety to provide the desired endoperoxide prostaglandin analogs. The reaction is straightforward. It involves only two significant steps. Moreover, it achieves significant yields in comparison with complex procedures of the prior art. In particular, yields as high as 80% in each of the reactions steps can be obtained, with the resulting overall yield as measured by the starting amount of terminal olefin being as high as 30–40%. This is considered quite high in prostaglandin synthesis techniques.

In accordance with the first step, the terminal olefin starting material is reacted to produce a pi-allylpalladium compound represented by the following reaction:

[Formula II]

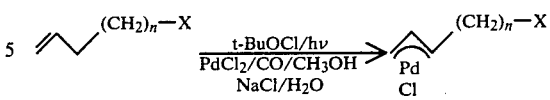

"X" and "n" are as defined above, and are selected by choice to prepare the desired prostaglandin endoperoxide analog.

The conversion of the terminal olefin to the pi-allylpalladium organic compound can be accomplished by two separate techniques, either of which is satisfactory. In the first technique, developed by the present inventor, and reported in *Synthetic Communications*, Vol. 9 on page 659 (1979), which is incorporated herein by reference, monosubstituted terminal olefins are converted to pi-allylpalladium compounds by an in situ allylic chlorination-palladation sequence shown above. The procedure may be effectively employed since it tolerates important organic functionality and also avoids the isolation of an intermediate allylic chloride.

In the reaction as described in the referenced literature article, the reaction flask is cooled in ice, and nitrogen gas is bubbled through the terminal olefin. t-Butyl hypochlorite is added as a chlorinating agent and the mixture is irradiated with a sun lamp for up to about 45 minutes at 0° C. Thereafter, the reaction mixture is poured into a vigorously stirred mixture of palladium chloride, sodium chloride, methanol and water. The system is flushed with carbon monoxide and maintained under an atmosphere of carbon monoxide for an 8 to 12 hour reaction period. The reaction mixture is then filtered, poured into water and extracted with chloroform. The combined chloroform extracts are washed with water and dried over anhydrous sodium sulfate, concentrated and hexane is added, and the pi-allylpalladium compound is obtained.

It is understood that the reaction conditions for this first step are not critical and may be manipulated within certain of the ranges and time periods specified. Ambient pressure is employed. The important factor is that the terminal olefin is converted to a pi-allylpalladium compound. A wide variety of reaction conditions could conceivably be utilized to arrive at this intermediate organopalladium compound.

A second, simpler and more preferred way of preparing the pi-allylpalladium compound has been found in reported literature, and has been successfully used in carrying out this first step of the present synthesis. For details with regard to this procedure, see B. M. Trost, and P. J. Metzner, J. Am. Chem. Soc., 102, 3572 (1980), which disclosure is incorporated herein by reference. The Trost and Metzner preparation is preferred because it can be run with stoichiometric amounts of olefin. It was found in running the allylic chlorination-palladation approach, large excesses of olefin were preferable. In the Trost, et al. synthesis which employs direct palladation with palladium trifluoroacetate, the desired pi-allylpalladium compound can be achieved in as high as 60% yield based on the olefin or palladium. This technique is therefore preferred and can be summarized in the following alternative first reaction.

[Formula II]

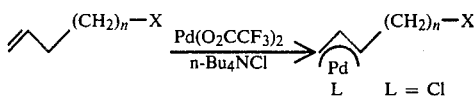

Again, "n" and "X" are as previously defined. Since this alternative reaction step is known as indicated in the referenced article, further details will not be provided. Again, the important factor is not the precise conditions employed, but merely that the reaction as exemplified in the referenced literature article is conducted to provide the pi-allylpalladium compound [II].

In the second step and first major part of the synthesis, compound [II] is added to a bicyclic olefin to provide a bicyclic alkylpalladium addition compound, as represented in the following addition reaction:

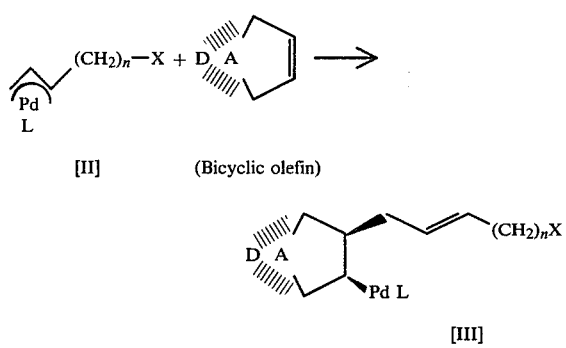

[II]   (Bicyclic olefin)

[III]

The reaction from compound [II] to compound [III] is a simple addition reaction allowing for addition of the pi-allylpalladium compound to the bicyclic olefin. Where the alternative and preferred first reaction step is employed, i.e., employing the palladium trifluoroacetate, the L moiety of the compound [II] is, of course, the more reactive trifluoroacetate group. It is preferred that L is a hexafluoroacetylacetonate ligand since it is more reactive and cleaner reactions result. Thus, where the original compound is a pi-allylpalladium halide (II, L=halide), it is desirable to exchange the chloride moiety with a hexafluoroacetylacetonate ligand since it is more reactive. This can be done by simply reacting the pi-allylpalladium halide with silver acetate and then with hexafluoroacetylacetone.

In the second step reaction where the pi-allylpalladium compound is added to the bicyclic olefin to form compounds of the skeletal structure [III], each of "n", "A" and "D" are as previously defined.

Once again, since the addition reaction between a pi-allylpalladium compound and a bicyclic olefin is known, see M. C. Gallazzi, et al., *Journal of Organometallic Chemistry*, 33, C. 45 (1971) and R. P. Hughes and Powell, *Journal of Organometallic Chemistry* 60, 387 (1973), details need not be given. This step in and of itself apart from the remainder does not constitute applicant's invention. These last mentioned two Journal articles are specifically incorporated herein by reference.

The third step and second and final major part of the process involves applicant's most important contribution to the synthesis route of prostaglandins. That step is the discovery that the palladium moiety of the addition product of a pi-allylpalladium compound and a bicyclic olefin can be effectively displaced with an acetylene moiety by reacting with any protected lithium acetylide [Formula IV] in the presence of two equivalents of triphenylphosphine to provide the skeletal structure of the endoperoxide prostaglandin analogs [Formula V]. It is represented by the following equation:

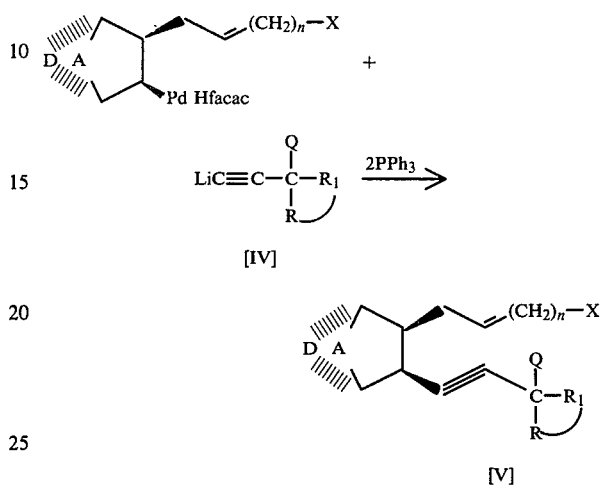

[IV]

[V]

If it is desired that one have only double bond unsaturation in Formula V, the lithium acetylide carbon to carbon triple bond can be reduced to a cis double bond in near quantitative yield by simple hydrogenation. To prepare the trans double bond structure, a lithium divinyl cuprate, or a trialkylvinylstannane, in triphenylphosphine can be used to replace [IV].

The third reaction step, begins by preparation of the lithium acetylide compound. The procedure is a known procedure for making lithium acetylides and is discussed in *The Chemistry of the Carbon-Carbon Triple Bond*, ed. S. Patai, J. Wiley and Sons, 1978, New York, which is incorporated herein by reference. For example, 1-octyn-3-ol-tetrahydropyranyl ether in tetrahydrofuran is deprotonated with normal butyl lithium to provide a representative compound of Formula [IV] of the following formula:

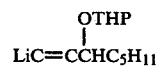

The acetylide displacement reaction is preferably begun at $-78°$ C. and allowed to warm to room temperature. Typically the temperature for this reaction may be from $-20°$ C. to $-78°$ C. The reaction times do not appear to be important, it merely being necessary that the ingredients are thoroughly mixed at low temperature. The reaction is preferably conducted in the presence of stirring. The reaction is conducted at low temperatures preferably, but it is all right to allow it to slowly warm to ambient conditions.

Pressure is not critical. The reaction is conducted in the presence of a solvent in order to allow intimate admixture of the reacting lithium acetylide [IV] and bicyclic olefin palladium addition compound, [III]. The precise solvent employed is not critical, but satisfactory results can be obtained with diethyl ether, and other standard aprotic solvents such as tetrahydrofuran and the like.

In the Formula last presented, the "OTHP" group is a representative protecting group of the "Q" moiety.

The reaction is a simple displacement reaction and forms the basic skeleton [V] of the desired endoperoxide analog. The amount that is obtained is in most instances from 30% to 40% of the starting olefin, a high yield for a complex prostaglandin synthesis technique.

As a final step, the blocking or protecting group, that is, "Q", is removed by conventional techniques. Specifically, for the OTHP group an ether cleavage can be accomplished by use of para toluenesulfonic acid in methyl alcohol. It is preferred that Q be OTHP, although it is not essential. Another protecting group is an ester which can be removed by conventional ester hydrolysis to provide the corresponding alcohol group. This can be accomplished in the presence of a strong base, such as potassium hydroxide in methyl alcohol. These techniques will be further demonstrated in the specific examples.

The following examples are offered to further illustrate but not limit the process and compounds of the present invention.

TABLE #1

EXAMPLES 1-11

| Exam. | A | B | D | n | X | Q | R | $R_1$ |
|---|---|---|---|---|---|---|---|---|
| 1. | $CH_2$ | C≡C | $CH_2CH_2$ | 3 | COOH | OH | H | $C_5H_{11}$ |
| 2. | $CH_2$ | C≡C | $CH_2CH_2$ | 3 | $CO_2CH_3$ | OH | H | $C_5H_{11}$ |
| 3. | $CH_2$ | C≡C | $CH_2CH_2$ | 7 | COOH | OH | H | $C_5H_{11}$ |
| 4. | $CH_2$ | C≡C | $CH_2CH_2$ | 7 | $CO_2CH_3$ | OH | H | $C_5H_{11}$ |
| 5. | $CH_2$ | C≡C | $CH_2CH_2$ | 0 | COOH | OH | H | $C_5H_{11}$ |
| 6. | $CH_2$ | C≡C | $CH_2CH_2$ | 0 | $CO_2CH_3$ | OH | H | $C_5H_{11}$ |
| 7. | $CH_2$ | C≡C | CH=CH | 3 | $CO_2CH_3$ | OH | H | $C_5H_{11}$ |
| 8. | $CH_2CH_2$ | C≡C | $CH_2CH_2$ | 3 | $CO_2CH_3$ | OH | H | $C_5H_{11}$ |
| 9. | $CH_2$ | C≡C | $CH_2CH_2$ | 4 | OH | OH | H | $C_5H_{11}$ |
| 10. | $CH_2$ | Cis, CH=CH | $CH_2CH_2$ | 3 | $CO_2CH_3$ | α-OH | H | $C_5H_{11}$ |
| 11. | $CH_2$ | Cis, CH=CH | $CH_2CH_2$ | 3 | $CO_2CH_3$ | β-OH | H | $C_5H_{11}$ |

In each of the above examples, compounds which are endoperoxide analogs of prostaglandins were prepared, with the compounds corresponding to the general formula [I]. Variations for moieties represented by A, B, D, n, X, Q and R and $R_1$ are represented in Table #1 above which shows the examples. In each of the examples, except the last two, that is 10 and 11, which involve hydrogenation of example #2 to provide the vinyl rather than the acetylene group for B, the procedures were not varied from the following generally described procedure.

In each instance, the alternative first reaction was employed wherein the starting terminal olefin was reacted with the palladium bis-trifluoroacetate in accordance with the procedure of the previously incorporated by reference Trost, et al. article. In particular, four millimoles of palladium bis-trifluoroacetate was added to 568 milligrams (4.0 millimoles) of the terminal olefin, methyl 6-heptenoate, in 60 milliliters of acetone. The mixture was stirred at room temperature for 30 minutes. Thereafter, 1.5 grams of tetra n-butylammonium chloride was added and stirred for 10 minutes. After filtration through diatomaceous earth the solvent was removed under vacuum. The residue was dried at high vacuum for one hour. The residue was taken up in a 1:1 mixture of hexane and ethyl acetate. The organic phase was decanted from a black sticky oil. After repeating the washing about three to four times, the combined phases were concentrated for filtration through 20 grams of silica gel, using hexane:ether in a 3:2 ratio as eluant. The pi-allylpalladium compound (Formula II) was collected as a yellow band and dried in high vacuum for several hours.

The pi-allylpalladium chlorides formed in the first reaction step were converted to the hexafluoroacetylacetonates in accordance with the following procedure. The pi-allylpalladium chloride dimer (Formula II, L=Cl) 1.4 millimoles was added to silver acetate (2.8 millimoles) in chloroform (50 milliliters). The mixture was stirred at room temperature for one hour and filtered to remove the silver chloride precipitate. Hexafluoroacetylacetone was added to the filtrate, stirred for 30 minutes, and the resulting solution was evaporated to dryness on a rotary evaporator. The yellow solid was freed of acetic acid by placing it under high vacuum for one hour.

Thereafter, in accordance with the second step of the sequence, the pi-allylpalladium compound now in the hexafluoroacetylacetonate form, was reacted with the bicyclic olefin on an equal molar basis, 2.8 millimoles of each, using methylene chloride solvent. The solution was stirred at room temperature for 24 hours, and with respect to examples 5-6 and 9, 48 hours, and then chromatographed on a florisil column using methylene chloride as the eluant. The compound [Formula III, L=Hfacac] was obtained as yellow crystals, after removal of the methylene chloride eluant on a rotary evaporator. The crystals were dried in a vacuum desicator for one hour. Example 5 gave an 84% yield. In Examples 3-4 and 9, the compounds were initially isolated as oils. Crystals were, however, obtained by dissolving the oils in warm methanol and cooling.

Pi-allylpalladium trifluoroacetates (Formula II, L=$O_2CCF_3$) can also be employed in this second step of the reaction sequence. As mentioned earlier, they can be prepared directly from the terminal olefin using the procedure of Trost and Metzner referenced earlier.

In the third major reaction step, the palladium moiety was displaced by anionic displacement with an acetylide anion. In particular, 3.28 millimoles of 1 octyn-3-ol tetrahydropyranyl ether in 7-10 milliliter of tetrahydrofuran was cooled to −78° C. It was deprotonated with 1.5 milliliter (3.67 millimoles) of approximately 2.45 normal butyl lithium. After stirring at −78° C. for 10 minutes, the mixture was allowed to warm up to −25° C. for 20 minutes, and then cooled to −78° C. again.

Thereafter, the palladium compound [Formula III, L=Hfacac] 3.10 millimoles was treated with 6 millimoles of triphenylphosphine in 20 milliliters of THF. The mixture was cooled to −78° C. and reacted with the cold lithium acetylide by addition via a syringe. The reaction mixture was kept at −78° C. for one hour, then at −25° C. for three hours before warming up to room temperature. After a total reaction time of 36 hours, the reaction was worked up in the following manner. The reaction mixture, usually black, but also varying between yellow-brown and black, was quenched at −78° C. with 1 milliliter of methyl alcohol. All solvent was then removed under vacuum. The residue was taken up in hexanes and fed through diatomaceous earth. Usually about 100 milliliter of hexanes was used. The combined hexane washings were washed with 2×50 milliliters water and 50 milliliters of 2 normal potassium carbonate. The organic layers were dried over anhydrous sodium sulfate and the solvent removed under vacuum. The reside was chromatographed on silica gel using a mixture of benzene-ethyl acetate, hexanes-ethyl acetate, or hexanes-ethylether as eluants.

In the described procedure 150 grams of silica gel was used with an eluant of benzene:ethylether, ratio of 19:1. The lithium acetylide it was noted could be added cold by syringe, dropwise, or it could be added in a one shot addition and no effect on yield was observed. The compound, having the desired skeletal structure, formula [V] is now prepared.

Thereafter, THP-ether clevage and ester hydrolysis occurred in the following manner. 240 Milligrams (0.54 millimoles) of THP-ether and 5 milligrams of para toluenesulfonic acid in 10 to 12 milliliters of methyl alcohol was heated under reflux for 30 minutes. The reaction mixture was then cooled and the solvent removed under vacuum. The residue was taken up in hexanes and the hexane layer washed three times with water or 2 normal potassium bicarbonate. The organic phase was dried over sodium sulfate, the solvent removed under vacuum and the residue chromatographed on 30 grams of silica gel using a 1:1 mixture of hexanes and ether.

In the case of the hydrolysis of the methyl ester, 0.75 millimoles of methyl ester was heated in 10 milliliters of methyl alcohol and 3 milliliters of 2 normal potassium hydroxide for 30 minutes. After cooling, the methanol was removed under vacuum, the residue taken up in ether, and the organic phase washed with sodium hydrogen sulfate followed by water, and then dried over sodium sulfate. The solvent was removed under vacuum, and the residue chromatographed on silica gel using hexane:ethyl ether in a 2:1 ratio as the eluant. The resulting products were analyzed by nuclear magnetic resonance, infrared analysis, melting point and % carbon-hydrogen analysis. In every instance, based upon the amount of original starting material, the product yield was within the range of 30% to 40% of the starting terminal olefin.

The compounds of Examples 10 and 11 wherein the B moiety involves a cis double bond, were prepared by hydrogenating the corresponding acetylenes using conventional hydrogenation procedures as previously described in the specification.

The compounds of Examples 1 through 11 were tested against arachidonic acid induced platelet aggregation. The compounds proved to be potent inhibitors of blood platelet aggregation as indicated by the following $EC_{50}$ values (concentration of agent necessary to reduce by 50% the in vitro blood platelet aggregation caused by addition of arachidonic acid).

The compounds of the present invention can be administered in parenteral or oral dosage forms over wide dose ranges, for example from about 0.05 mg/kg to about 10 mg/kg.

TABLE #2

| BIOLOGICAL TEST DATA | |
|---|---|
| Example | EC 50 vs Arachidonic Acid |
| 1. | 45 (ng/ml) |
| 2. | 70 (ng/ml) |
| 3. | 1000 (ng/ml) |
| 4. | 400 (ng/ml) |
| 5. | 4000 (ng/ml) |
| 6. | 8000 (ng/ml) |
| 7. | 3600 (ng/ml) |
| 8. | 5800 (ng/ml) |
| 9. | 3600 (ng/ml) |
| 10. | 5000 (ng/ml) |
| 11. | 8000 (ng/ml) |

For comparison $PGE_1$ gave an EC 50 of 18 ng/ml and prostacyclin 4 ng/ml. It appears that the compounds prepared in accordance with this invention are specific inhibitors of thromboxane synthetase.

These compounds were studied in vivo in an animal model for experimental thrombosis. The use of this model is described in detail in the reprint, Use of the Biolaser in the Evaluation of Anti-Thrombotic Agents, J. S. Fleming et al. "Platelets and Thrombosis", eds. S. Sherry and A. Scriabrine, University Park Press, 1974, Baltimore, which is incorporated herein by reference.

In brief, a micro-injury is created by a laser beam focused through a microscope onto the endothelium surface of a small blood vessel in a surgically implanted ear chamber of a rabbit. The injury induces the rapid formation of a platelet thrombis which can be measured. Compounds which are potent inhibitors of platelet aggregation (e.g., prostacyclin or anagrelide) produce a significant inhibition of this kind of thrombosis. Prostacyclin is active in the biolaser model when infused intraveneously. The results of these tests preliminarily indicate that there is a super additive interaction between anagrelide and the compounds of this invention. Thus, when the example 2 compound was combined with anagrelide even with the anagrelide at a lower than threshold level, there is nevertheless a substantial reduction in thrombosis noted. To date, no other compounds have undergone significant in vivo analysis in the rabbit ear test. However, all have undergone the in vitro testing previously described, and have been shown to be active against arachidonic acid induced platelet aggregation.

What is claimed is:

1. A method of synthesis of prostaglandin analogs by the addition of pi-allyl-palladium compounds to bicyclic alkenes, said method comprising:
    converting a terminal olefin of the formula:

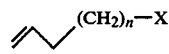

to a pi-allyl-palladium compound of the formula

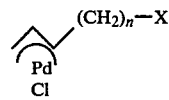

wherein "n" equals a whole integer of from 0 to 7 and "X" is carboxylic acid, or $C_1$–$C_8$ ester, alcohol, ether or amide groups;
adding said pi-allyl-palladium compound to a bicyclic olefin of the formula

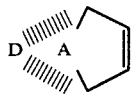

wherein "A" is methylene, ethylene, oxy, imino, or lower alkyl, phenyl, or aryl, substituted amino; and "D" is methylene, ethylene, vinylene, methyleneoxy, alkylidenedioxy, iminooxy, dithio or azo, to provide a bicyclic alkyl palladium addition compound, displacing the palladium moiety of said addition compound with an acetylene or vinyl moiety, and removing the protecting groups, if any exist, from the acetylene or vinyl moiety, to provide a prostaglandin analog.

2. A method of synthesis of prostaglandin analogs from bicyclic alkylpalladium addition compounds of the following formula:

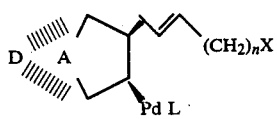

wherein L represents either a halogen, Hfacac, or $O_2CCF_3$, said method comprising:

reacting the compound of Formula III with a lithium acetylide compound of the formula:

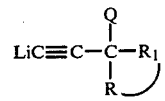

wherein A is methylene, ethylene, oxy, imino, or alkyl, phenyl or aryl substituted imino; D is methylene, ethylene, vinylene, methyleneoxy, alkylidenedioxy, iminooxy, dithio, or azo; n. equals a whole integer of from 0–7, X is carboxylic acid, or $C_1$–$C_8$ ester, alcohol, ether or amide groups; R and $R_1$ are hydrogen, lower alkyl and lower aryl or $(CH_2)_z$ with Z being 2–5; and Q is hydroxy, methoxy, acetoxy or hydrogen or Q and R are oxa.

3. The method of claim 1 wherein said terminal olefin is converted to a pi-allylpalladium compound by an in situ allylic chlorination-palladation sequence.

4. The method of claim 1 wherein said terminal olefin is converted to a pi-allylpalladium compound by direct palladation with palladium trifluoroacetate.

5. The process of claim 2 wherein R equals hydrogen and $R_1$ is $C_5H_{11}$.

6. The process of claim 2 wherein Q is hydroxyl.

7. The process of claim 2 wherein n equals 3.

* * * * *